(12) United States Patent
Tyler

(10) Patent No.: US 8,236,052 B2
(45) Date of Patent: *Aug. 7, 2012

(54) DEVICE AND METHOD FOR INCREMENTAL CORRECTION OF SIGHT DISORDERS AND OCULAR DISEASES

(76) Inventor: Thomas D. Tyler, San Carlos, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/607,275

(22) Filed: Oct. 28, 2009

(65) Prior Publication Data

US 2010/0049176 A1   Feb. 25, 2010

Related U.S. Application Data

(63) Continuation of application No. 09/564,525, filed on May 4, 2000, now Pat. No. 7,635,388.

(51) Int. Cl.
A61F 2/14 (2006.01)
A61B 18/18 (2006.01)
(52) U.S. Cl. .............................. 623/4.1; 606/5
(58) Field of Classification Search .................. None
See application file for complete search history.

(56) References Cited

U.S. PATENT DOCUMENTS

| | | |
|---|---|---|
| 4,461,294 A | 7/1984 | Baron |
| 4,549,529 A | 10/1985 | White |
| 4,575,373 A | 3/1986 | Johnson |
| 4,603,697 A | 8/1986 | Kamerling |
| 5,171,266 A | 12/1992 | Wiley et al. |
| 5,296,881 A | 3/1994 | Freeman |
| 5,300,118 A | 4/1994 | Silvestrini et al. |
| 5,354,331 A | 10/1994 | Schachar |
| 5,459,133 A | 10/1995 | Neufeld |
| 5,465,737 A | 11/1995 | Schachar |
| 5,503,165 A | 4/1996 | Schachar |
| 5,520,631 A | 5/1996 | Nordquist et al. |

(Continued)

FOREIGN PATENT DOCUMENTS

FR 2784287 A1 * 4/2000

(Continued)

OTHER PUBLICATIONS

Heneger, et al., *Inv Ophth* 31 (8):1644-1646, 1990.

*Primary Examiner* — David H Willse
*Assistant Examiner* — Javier Blanco
(74) *Attorney, Agent, or Firm* — Dickstein Shapiro LLP

(57) ABSTRACT

A device and method of use thereof for incrementally adjusting the size and/or shape of a particular body part is provided. The device comprises first and second layers each formed of a synthetic resin. The first layer is formed of a heat-shrinkable material having a low melting point while the second layer has a melting point much higher than the first layer. Upon being subjected to energy, the first layer will shrink or contract causing the second layer, and thus the overall device, to bend in the direction of contraction. In use, the device is inserted into the particular body part after which energy is applied to the device so as to cause the body to expand, move, reshape, etc. The invention is particularly useful for treatment of accommodative disorders of the eye by positioning one or more of the devices within the eye sclera or attached to the sclera around the limbus so that the sclera and ciliary body are expanded away from the crystalline lens upon being of the device.

4 Claims, 1 Drawing Sheet

U.S. PATENT DOCUMENTS

| | | |
|---|---|---|
| 5,529,076 A | 6/1996 | Schachar |
| 5,533,997 A | 7/1996 | Ruiz |
| 5,645,583 A | 7/1997 | Villain et al. |
| 5,722,952 A | 3/1998 | Schachar |
| 5,803,923 A | 9/1998 | Singh-Derewa et al. |
| 5,820,624 A | 10/1998 | Yavitz |
| 5,824,086 A | 10/1998 | Silvestrini |
| 5,855,604 A | 1/1999 | Lee |
| 5,876,439 A | 3/1999 | Lee |
| 5,888,243 A | 3/1999 | Silvestrini |
| 5,919,228 A | 7/1999 | Hennig |
| 5,928,129 A | 7/1999 | Ruiz |
| 5,944,752 A | 8/1999 | Silvestrini |
| 6,006,756 A | 12/1999 | Shadduck |
| 6,007,578 A | 12/1999 | Schachar |
| 6,051,023 A | 4/2000 | Kilmer et al. |
| 6,066,170 A | 5/2000 | Lee |
| 6,096,076 A | 8/2000 | Silvestrini |
| 6,096,078 A | 8/2000 | McDonald |

FOREIGN PATENT DOCUMENTS

| | | |
|---|---|---|
| WO | WO 9749354 A1 * | 12/1997 |

* cited by examiner

DEVICE AND METHOD FOR INCREMENTAL CORRECTION OF SIGHT DISORDERS AND OCULAR DISEASES

RELATED APPLICATION

The present application is a continuation of application Ser. No. 09/564,525 filed May 4, 2000 now U.S. Pat. No. 7,635,388. The priority of the prior application is expressly claimed, and the disclosure of the prior application is hereby incorporated by reference in its entirety.

BACKGROUND OF THE INVENTION

1. Field of the Invention

The present invention is broadly concerned with a device which can be implanted in a body part (e.g., eye, tissue, artery) and methods of externally manipulating the device to adjust or alter the configuration of the body part. More specifically, the invention is directed towards the use of that device to adjust the curvature of the sclera of the eye so as to alter functional ocular structural relationships (e.g., such as to restore the accommodative ability of the eye), thus treating various eye conditions.

2. Description of the Prior Art

In order for the eye to clearly see an object at a distance of about twenty feet or greater, the object must be focused on the retina of the eye. When this occurs in the relaxed state of the eye, it is referred to as "emmetropia." If the focal point is anterior to the retina, it is classified as "myopic." On the other hand, if the focal point is behind the retina, it is classified as "hyperopic."

Refractive correction is required to correct these focusing errors. This has typically been accomplished by the natural lens or by medical or surgical refractive devices. However, after the eye has been made to correctly focus on an object at a distance, it must then be capable of changing its refractive ability to see an object as it comes nearer the eye. This is accomplished physiologically through changes in the natural lens referred to as accommodation.

The ocular structures involved in accommodation include filaments inserted onto the lens equator and called zonules or zonular fibers. The zonules are connected to the ciliary body which is a muscle attached to the sclera that encircles and thus, in cooperation with the zonules, suspends the eye's lens. The actual mechanism by which these structures influence accommodation is still highly debated, but includes changes in lens shape and position with subsequent change in the overall refractive power of the eye.

Loss of accommodative ability, or presbyopia, occurs naturally with aging. It becomes noticeable at about forty years of age, and consistently worsens until about seventy years of age, at which time accommodation is effectively nonexistent. Theories concerning the causes of the loss of accommodative ability include increasing rigidity of the lens or its capsule, lens enlargement, laxity of the zonules, aging of the ciliary body, and combinations of the foregoing.

The usual way to correct this problem is to use bifocal lenses. However, some people dislike wearing glasses, particularly bifocals, for various reasons. One problem with bifocal lenses is that they present lines where the two portions of the lens are joined together. Furthermore, people must become accustomed to reading through one relatively small portion of the lens, while looking at distant objects through a different portion of the lens. Bifocal glasses also have the same disadvantages present in regular glasses. Such disadvantages include the fact that the glasses are breakable, become fogged when coming in from the cold, steam up in hot weather, and require frequent cleaning.

Other treatments have been attempted to correct presbyopia. For example, U.S. Pat. Nos. 5,928,129 and 5,802,923 each disclose the production of "bifocal-like" refractive correction through laser ablation of the inferior cornea.

Treatment methods have attempted to return the accommodative ability to a presbyope via expansion of the scleral radius in the vicinity of the ciliary body by a scleral expansion band (U.S. Pat. No. 5,489,299) or by a band which is adjustable at the time of placement (U.S. Pat. No. 5,354,331). Some methods have even shortened the zonules connecting the ciliary body to the lens by enzymes, heat, radiation, or surgical repositioning of the ciliary body.

Adjustable, ocular refractive devices for use in the cornea have been developed as well. Such adjustable devices include those which are adjustable at the time of placement. For example, U.S. Pat. No. 5,681,869 describes a poly(ethylene oxide) gel that is injected into the cornea in an amount sufficient to produce the required refractive correction. Additionally, U.S. Pat. No. 5,489,299 discloses a length-adjustable scleral expansion band for treatment of presbyopia, with the band length being measured and set at the time of placement. U.S. Pat. No. 5,919,228 discloses a corneal ring comprised of a memory metal that, upon insertion into the cornea, is caused to reach a temperature at which it assumes a prior impressed shape thus altering the shape of the cornea.

Other prior art devices include those which require further surgery to modify them if necessary after placement. For example, U.S. Pat. No. 5,855,604 discloses a hollow device placed into the cornea stroma. The device includes quantities of strands which may be removed at the time of placement, or which may be removed or added by surgery as needed after placement.

Each of the foregoing prior art techniques attempted thus far are lacking in that they only correct presbyopia at one particular stage of the disorder. Thus, as the condition worsens, the treatment would need to be repeated or otherwise enhanced. Or, in case of adjustable devices, additional surgery is needed to make the desired modifications. All of this poses undue risk to the eyes with each successive treatment.

SUMMARY OF THE INVENTION

The present invention overcomes the problems of the prior art by broadly providing a device and method of using the device which allows for a single surgical device implantation and successive, incremental adjustments of the device as necessary through externally applied energy.

In more detail, the inventive device comprises a first shrinking layer formed of a synthetic resin and a second bending layer formed of a synthetic resin and attached to said first layer. Optionally, a third barrier layer can be attached to the first shrinking layer to assist in dissipating the energy applied to the device.

Advantageously, the device is designed so that, upon the application of energy (e.g., laser energy) thereto, the first layer will shrink or contract as it melts, thus pulling the second layer to provide directional bending of the device. Because the second layer has a higher melting point (and often a lower melt index) than the first layer, it remains substantially free of shrinking during this process:

According to the inventive methods, the device is placed within a body part (e.g., an eye) whose size or shape is to be altered. Once the device is inserted, energy is applied (preferably externally) to the device causing it to bend as described above. As the device bends, it will cause the body part to likewise expand or move in the area surrounding the device.

After the application of energy to the device, measurements can be taken to determine whether sufficient expansion or movement has occurred, depending upon the desired treatment for which the inventive method is being utilized. If more expansion or movement is necessary, then additional energy can be applied to the device, and the measurements taken again. The foregoing steps can be repeated as many times as necessary until the desired result is obtained. Furthermore, the steps can be repeated long after the device has been inserted as further adjustments become necessary. The foregoing device and method is particularly useful for treating eye conditions such as presbyopia, hyperopia, glaucoma, and ocular hypertension.

DETAILED DESCRIPTION OF THE PREFERRED EMBODIMENTS

Figure 1:
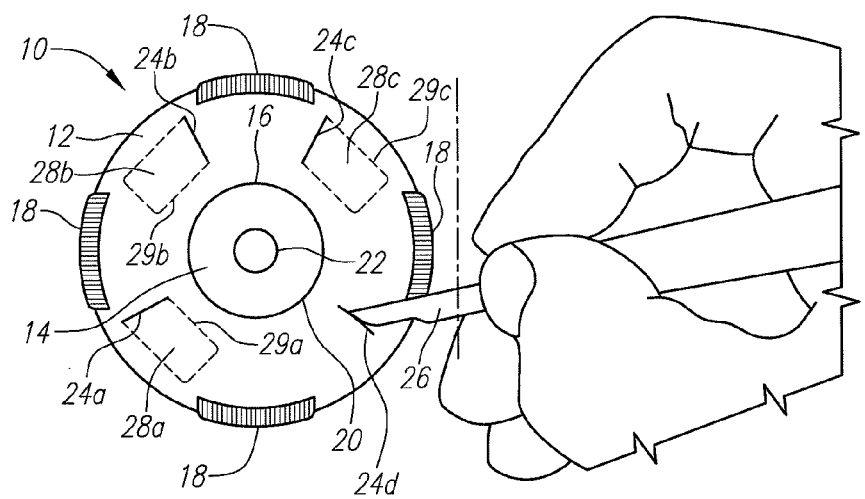
FIG. 1 is a plan view of an eye depicting the formation of scleral pockets during surgery according to the inventive methods.

Turning now to the figures, an eye 10 is depicted in FIG. 1. The eye 10 comprises a white, tough sclera 12 which encompasses most of the globe and a transparent cornea 14, which constitutes the anterior segment of the outer coat. The circular junction of the cornea 14 and the sclera 12 forms a limbus 16. External rectus muscles 18 control the movement of the eye 10.

The remaining internal components of the eye are not shown in the accompanying figures, but are well known to those skilled in the art. Briefly, the eye 10 contains a natural crystalline lens enclosed in a thin, membranous capsule located immediately posterior to the iris 20, suspended centrally posterior to the pupil 22 on the optical axis of the eye. The lens is suspended by zonules extending between the lenses capsule (at the equator of the lens) and the ciliary body. The ciliary body lies just under the sclera 12 (i.e., just inwardly of the sclera) and is attached to the inner surface of sclera 12. The foregoing internal workings of the human eye are described and illustrated in detail in U.S. Pat. No. 6,007,578, incorporated herein by reference.

Figure 2:
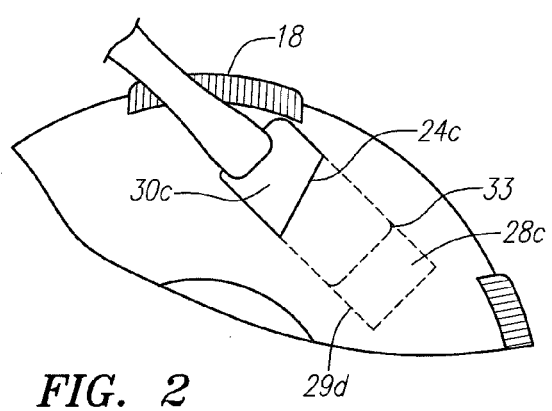
FIG. 2 is an enlarged fragmentary view showing the insertion of the inventive device into a scleral pocket formed in FIG. 1.

According to the inventive process, a scalpel 26 is used to make incisions 24a-d in the sclera 12 at a depth of from about ⅓ to about ½ the depth of sclera 12 (i.e., at a depth of from about 280-320 μm, and preferably about 300 μm). The incisions 24a-d are made adjacent to the rectus muscle insertions 18 approximately over the region of the ciliary body. Scleral pockets 28a-d are then formed at this depth by advancing the scalpel 26 towards the next adjacent rectus muscle insertion 18. At their nearest point, the respective inner edges 29a-d of the pockets 28a-d should be a distance of from about 0.5-3.5 mm. and preferably about 2 mm posterior to the limbus 16. A device 30a-d according to the invention is then inserted into each respective pocket 28a-d (see FIG. 2). Each of the incisions 24a-d are closed with sutures 32 (which may be "hidden" in the closed pockets) so that the devices 30a-d are completely enclosed within their respective pockets 28a-d and at least partially overlie the ciliary body. There is substantially no scleral radius expansion produced by the device at this point in the process.

Figure 4:
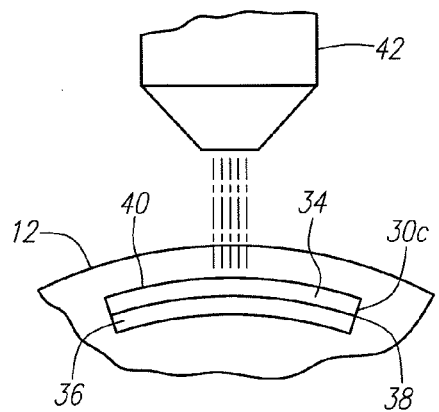
FIG. 4 is a cross-sectional view taken along line 4-4 of the eye of FIG. 3, depicting the cross-section of the inventive device and illustrating the application of energy to the device.
Figure 3:
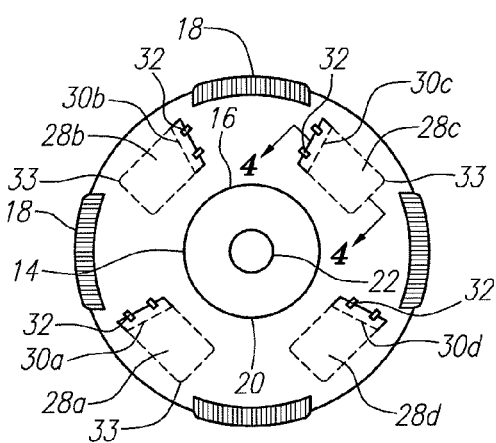
FIG. 3 is a plan view of the eye of FIG. 1 with a device according to the invention implanted in each of the previously formed scleral pockets.
Figure 5:
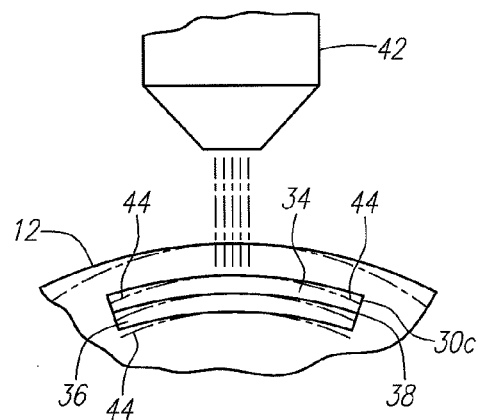
FIG. 5 is a view similar to that of FIG. 4, depicting the change in curvature of the device and the sclera after the application of energy to the device.

Device 30c is shown in vertical cross-section in FIGS. 4-5. In more detail, the depicted device 30c comprises a low melting point, shrinking layer 34 and a high melting point, bending layer 36 posterior to shrinking layer 34. Each of layers 34, 36 is moderately curved and abuts against the other so that the curvature of device 30 substantially corresponds to the curvature of the sclera 12. Furthermore, in the embodiment shown, devices 30a-d include optional "notched" corners 33 which would allow for anchoring of the device with sutures either to the scleral surface or within the scleral pocket(s).

Shrinking layer 34 is preferably formed of a low melting point, non-toxic material which is heat-shrinkable. Thus, Layer 34 should be formed of a material having a melting point of less than about 100° C., preferably from about 45-60° C., and more preferably from about 50-55° C. In some embodiments, layer 34 should be formed of a material having a melt index of at least about 4.5 g/10 min., preferably from about 6.3-26.0 g/10 min., and more preferably from about 6.3-15.0 g/10 min. (at an extrusion pressure of 2.16 kg and a temperature of 190° C. as defined by ASTM D-1238). A particularly preferred material for use as layer 34 is a polymethylmethacrylate (PMMA) or a mixture of polymethylmethacrylates wherein the polymethylmethacrylate or mixture thereof has the described melting point and/or melt index. A particularly preferred polymethmethacrylate for use as shrinking layer 34 is sold under the name ICI 924 CL (available from ICI Acrylics, Inc.).

Bending layer 36 is preferably formed of a high melting point, non-toxic material which is bendable, but will not readily shrink upon heat application. Thus, bending layer 36 should be formed of a material having a melting point of at least about 45° C., preferably from about 60-100° C., and more preferably from about 70-80° C. In some embodiments, layer 36 should be formed of a material having a melt index of less than about 4.4 g/10 min., preferably from about 1.1-4.4 g/10 min., and more preferably from about 1.1-2.2 g/10 min (at an extrusion pressure of 2.16 kg and a temperature of 190° C. as defined by ASTM D-1238). Similar to shrinking layer 34, a particularly preferred material for use as bending layer 36 is a polymethylmethacrylate or a mixture of polymethylmethacrylates wherein the polymethylmethacrylate or mixture thereof has the described melting point and/or melt index. A particularly preferred polymethylmethacrylate for use as bending layer 36 is sold under the name ICI 1000 ECL (available from ICI Acrylics, Inc.).

In another embodiment, the ASTM D-1238 melt index of shrinking layer 34 is at least about 2 times, preferably at least about 4 times, and more preferably from about 6-26 times greater than the ASTM D-1238 melt index of bending layer 36. In another embodiment, the melting point of bending layer 36 is at least about 5° C., preferably at least about 10° C., and more preferably from about 20-30° C. greater than the melting point of shrinking layer 34.

Other types of materials (both synthetic and natural resins as well as plastics formed from these resins) can be utilized to form shrinking layer 34 or bending layer 36. Other suitable synthetic resins include polyethylene, polypropylene, polyvinyl chloride, and polytetrafluorine. It may also be desirable to incorporate certain agents into the layers, depending upon the application. Such agents include physiologically acceptable metals (e.g., titanium, gold, platinum, tantalum, stainless steel), ceramics, porcelain, alumina, silica, silicon carbide, glass.

It will be appreciated that the melting point of either shrinking layer 34 and/or bending layer 36 can be modified by the addition of a compound to alter the melting point of the particular layer. Examples of such compounds include carbon black, indocyanine green, methylene blue, titanium oxide, because they preferentially absorb energy at certain energy wavelengths. In particularly preferred embodiments, shrinking layer 34 is formed of a material which comprises from about 0.1-2.0% by weight titanium oxide, and preferably from about 0.25-0.75% by weight titanium oxide, based upon the total weight of the material taken as 100% by weight. Of course, those skilled in the art will appreciate that the type and quantity of energy-absorbing dye utilized can be altered depending upon the desired application.

The device 30c is preferably formed by co-extruding the materials of which the respective layers are formed, but may also be formed by bonding the layers together through solvents, pressure, or other physical methods. Regardless, layers 34, 36 will be bonded to one another at location 38 so as to form device 30c. A barrier layer (not shown) can also be applied to the outer surface 40 of shrinking layer 34 to protect the tissue adjacent layer 34 from damage during heating thereof. The barrier layer should also be formed of a high melting point, bendable material such as those described with respect to bending layer 36.

In the embodiment depicted, shrinking layer 34 has a thickness of from about 0.125-1.50 mm, and preferably from about 0.25-0.75 mm, while bending layer 36 has a thickness of from about 0.125-1.50 mm, and preferably from about 0.50-1.00 mm. Furthermore, the width of the illustrated devices 30a-d at their respective widest points is from about 1.0-4.0 mm, and preferably from about 1.5-3.0 mm. In embodiments where devices 30a-d are curved, the radius of curvature should be from about 7-10 mm so that the curve is substantially similar to the curvature of most human sclera at the site of device placement. Finally, it is preferred that the length of the devices 30a-d at their respective longest points be such that the devices 30a-d can fit into a sclera pocket 28a-d having a length of from about 3-8 mm, and preferably about 4.5 mm.

After placement of the devices 30a-d, the accommodative ability of the eye is measured according to known methods (e.g., by measuring the accommodative amplitude or by stigmatoscopy). External energy is then applied to each of the devices 30a-d. The source of energy is not critical, so long as it can be applied with sufficient intensity to cause layer 34 to shrink or contract. At the same time, the energy should be provided with a sufficiently low intensity so as to minimize, and preferably prevent, layer 36 from melting or shrinking as well as to avoid damage to the eye tissue surrounding the devices 30a-d.

Types of energy sources which can be utilized include UV sources, IR sources, radio frequency emitters, heat, and low voltage DC and low voltage high frequency sources. However, the most preferred energy source is a laser 42 of the type typically utilized by an opthalmologic surgeon. The identity, intensity, and duration of the application of the laser used to adjust the devices 30a-d can be readily selected by a person of ordinary skill in the art. Preferred lasers include diode IR (which have a wavelength of about 805 nm) and argon (argon blue which has a wavelength of about 488 nm, argon green which has a wavelength of about 514.5 nm, or a combination of the two) lasers. However, any of the following lasers can be used as well: carbon dioxide; helium-neon; helium-cadmium; argon ion; krypton ion; xenon ion; nitrous oxide; iodine; holmium-doped yttrium-aluminum garnet; yttrium lithium fluoride; excimer; chemical; harmonically oscillated; dye; nitrogen; neodymium; erbium; ruby; and titanium-sapphire. With any of these types of lasers, the duration of treatment is typically from about 0.5-5.0 seconds while focusing on a location having a diameter of from about 300-500 µm.

After energy treatment, the accommodative ability of the eye 10 is again measured to determine whether further energy treatment is necessary. If it is, additional energy is applied as described above, and the accommodative ability is again measured with these steps being repeated as needed until the desired accommodation is obtained.

Referring to FIGS. 4-5 it can be seen that the use of laser 42 to apply energy to shrinking layer 34 causes layer 34 to melt, and thus shrink or pull in a direction away from layer 36, causing layer 35 to pull toward layer 34. This "pulling" causes controlled, directional bending of the device 30c and, in turn, of the sclera 12. As the shrinking of layer 34 causes the device 30c to bend in a direction away from the eye, the sclera is expanded away from the lens so as to increase the effectiveness of the accommodative apparatus of the eye. Phantom lines 44 in FIG. 5 depict the curvature of layers 34, 36 and sclera 12 prior to energy application.

Advantageously, unlike prior art devices, devices according to the instant invention can be adjusted after placement thereof without subjecting the patient to further surgery. Thus, as the presbyopic condition worsens over time (e.g., about 2 years to 10 years after insertion), the patient can return to the surgeon who inserted the device, or to any other surgeon with an available energy-applying apparatus, and have the device further adjusted until acceptable accommodative levels are achieved.

It will be appreciated that in some applications direct application of energy to layer 34 may create problems (e.g., pitting, bubbling, or irregular melting of the shrinking layer 34). In these instances, it is generally desirable to apply the energy to bending layer 36, allowing it to be an energy source for the less tolerant shrinking layer 34. This allows for a more uniform heat dispersion along and through shrinking layer 34, thus minimizing or avoiding problems with the material of shrinking layer 34 as well as minimizing or substantially preventing damage to the surrounding tissue.

The potential amount of shrinkage available to shrinking layer 34 can be increased during manufacturing by stretching or pulling the material of which shrinking layer 34 is formed prior to cooling and hardening. This will result in an increase in the amount of stress energy of the material and thus an increase in the material shrinkage. Additionally, the shrinkage can be controlled by the selection of the melt index of the material.

While the invention has been discussed with respect to the use of generally rectangular, slightly curved devices 30a-d in an eye 10 for treatment of presbyopia, it should be understood that the invention is not so limited. For example, the size and shape of device 30 can be altered depending upon the shape and location of the area in which it will be used. Thus, device 30 can be configured to alter the physical geometry of other human or animal body parts (e.g., tissues, organs, veins, arteries, etc.) as necessary to treat a particular condition. Furthermore, rather than several small segments of the device, one larger or ringed segment could be utilized, as well as flat panels with adjustable vanes or flaps to act as valves.

The inventive device could also be used to open blocked veins or arteries by placing the device on or within the vein or artery and applying energy to the device so that directional bending occurs, thus expanding or closing the vein or artery. Advantageously, the invention allows for incremental expansion or closure of the vein or artery with subsequent additional expansion or closure being possible as needed. The device could also be used to incrementally increase or decrease the flow of fluid from the brain through a shunt in a patient suffering from hydrocephalus.

Although the inventive device has been discussed as a treatment for presbyopia, it can be used to treat any eye condition which is treatable by changing the shape or positions of the component structures of the eye and their functional relationship to each other. The device can also be used in eye drainage valves which bypass the trabecular meshwork. This would be accomplished by inserting a closed valve having the device disposed therein, and incrementally subjecting the device to applied energy so that the valve is opened or closed by small degrees until the desired flow level is obtained.

Furthermore, the device could be used to treat myopia or hyperopia by utilizing a ring-shaped device or partial ring-shaped devices (e.g., 140° rings). In this embodiment, the devices would be inserted into the cornea with the shrinking layer facing outwardly from the eye so that the cornea is "flattened" upon shrinkage of the device to treat myopia. To treat hyperopia, the devices would be inserted into the cornea with the shrinking layer facing inwardly from the eye. The non-shrinking layer is necessary to give directional control of the bending as well as to act as an energy source for the melting layer.

Finally, although the illustrated embodiment depicts a device according to the invention inserted in a sclera pocket, it should be understood that it may be desirable to attach the device to the surface of the body part to be treated. For example, the device could be sutured or glued with a biocompatible adhesive to the outer surface of the sclera.

EXAMPLES

A device according to the invention was formed by co-extruding two PMMA layers. A first layer was formed of PMMA having an ASTM D-1238 melt index of 1.1 and carbon black dye added thereto. A second layer was formed of PMMA having an ASTM D-1238 melt index of 6.6 and having titanium oxide added thereto. Five devices were formed with the following dimensions, respectively: two samples each designated as Sample 1-0.33 mm×0.66 mm×10 mm; and two samples each designated as Sample 2 and one sample designated as Sample 3-0.66 mm×0.66 mm×10 mm.

Multiple diode laser treatments were carried out by subjecting the first layer (having a black dye incorporated therein) of one specimen of each of Samples 1 and 2 to laser energy and then repeating the energy application to the second layer (having a white dye incorporated therein) of the same specimens of Samples 1 and 2. With Sample 3, the first layer (having a black dye incorporated therein) followed by the second layer (having a white dye incorporated therein) was subjected to multiple laser applications along its length, with the direction of bend and change in length being noted.

The laser parameters were chosen to maximize the change in shape of the device while minimizing focal deformity. The length of each sample was determined (with Vernier Callipers) after the first, third, fifth, seventh, and ninth laser treatments. These results are reported in Tables 1-3. The direction of bend was either toward the first or black layer (designated "B") or toward the second or white layer (designated "W").

TABLE 1

Sample 1 (0.33 × 0.66 mm Specimens)

|  | Laser Application | Laser Application |
|---|---|---|
| Intensity (mW) | 60 | 50 |
| Spot Size (microns) | 300 | 500 |
| Duration (milliseconds) | 5000 | 9000 |

| Laser Treatment | Applied To Black (first layer) Length Change (mm) | Bend Direction | Applied To White (second layer) Length Change (mm) | Bend Direction |
|---|---|---|---|---|
| 1$^{st}$ | .000 |  | .020 | B |
| 3$^{rd}$ | .005 | B | .030 | B |
| 5$^{th}$ | .010 | B | .050 | B |
| 7$^{th}$ | .010 | B | .075 | B |
| 9$^{th}$ | .015 | B | .090 | B |
| Total Change (mm) | 0.015 | B | 0.90 | B |

TABLE 2

Sample 2 (0.33 × 0.66 mm Specimens)

|  | Laser Application | Laser Application |
|---|---|---|
| Intensity (mW) | 50 | 160 |
| Spot Size (microns) | 500 | 300 |
| Duration (milliseconds) | 9000 | 9000 |

| Laser Treatment | Applied To Black (first layer) Length Change (mm) | Bend Direction | Applied To White (second layer) Length Change (mm) | Bend Direction |
|---|---|---|---|---|
| 1$^{st}$ | .010 |  | .005 | W |
| 3$^{rd}$ | .015 | B | .035 | W |
| 5$^{th}$ | .015 | B | .055 | W |
| 7$^{th}$ | .015 | B | .085 | W |
| 9$^{th}$ | .020 | B | .110 | W |
| Total Change (mm) | 0.20 | B | 0.110 | W |

TABLE 3

Sample 3 (0.66 × 0.66 mm Specimen)

|  | Laser Application |
|---|---|
| Intensity (mW) | 60 |
| Spot Size (microns) | 500 |
| Duration (milliseconds) | 6000 |

| Laser Treatment # | Applied To Black (first layer) Length Change | Bend Direction |
|---|---|---|
| 7$^{th}$ | .015 | B |
| Intensity (mW) | 320 |  |
| Spot Size (microns) | 300 |  |

TABLE 3-continued

| Sample 3 (0.66 × 0.66 mm Specimen) | | |
| --- | --- | --- |
| Duration (milliseconds) | 500 | |
| Laser Treatment # | Applied To White (second layer) | |
| 7$^{th}$ | 0.290 | W |

I claim:

1. In a system comprising intrascleral prostheses, the improvement comprising:
    a plurality of incrementally adjustable intrascleral prostheses for implantation in the sclera of an eye to improve the accommodative ability of the eye,
    said prostheses having a first arcuate layer comprising a synthetic resin and a second arcuate layer comprising a synthetic resin, said layers being attached to each other and substantially coextensive and having different shrinkage characteristics when heated, one of which layers is a shrinking layer and the other of which is a bending layer such that said shrinking layer is capable of bending said bending layer upon the application of energy, the curvature of said layers being substantially similar to the curvature of a human sclera and having a convex surface and a concave surface such that said convex surface is adapted to face in the anterior direction of the eye and said concave surface is adapted to face in the posterior direction of the eye when said prostheses are implanted in the eye; and
    a source of energy capable of causing said prostheses to change shape, the source of energy selected from the group consisting of laser energy, UV sources, IR sources, radio frequency emitters, heat, and low voltage DC and low voltage high frequency sources;
    wherein said prostheses are operable to assume a first radius of curvature at a selected temperature, and to bend upon the application of energy in a manner which causes them to assume a second radius of curvature which will increase the effectiveness of the accommodative apparatus of the eye when the prostheses are implanted with their convex surfaces facing anteriorly and their concave surfaces facing posteriorly, said second radius of curvature being different than said first radius of curvature.

2. The system of claim 1 wherein each prosthesis is generally rectangular.

3. The system of claim 1 wherein each prosthesis is capable of undergoing a change in radius of curvature when exposed to sufficient energy to cause the shrinking layer to shrink.

4. The system of claim 1 wherein said prostheses are of sufficient size and shape to adjustably improve the accommodative ability of the eye.

* * * * *